United States Patent [19]
Keuhn, Jr. et al.

[11] Patent Number: 5,374,262
[45] Date of Patent: Dec. 20, 1994

[54] ADJUSTABLE GARMENT ATTACHMENT SYSTEM

[75] Inventors: Charles P. Keuhn, Jr.; David A. Kuen, both of Neenah; Neal A. Rollins, Menasha; Alan F. Schleinz, Appleton, all of Wis.

[73] Assignee: Kimberly-Clark Corporation, Neenah, Wis.

[21] Appl. No.: 998,961

[22] Filed: Dec. 30, 1992

[51] Int. Cl.$^5$ .................. A61F 13/15; A61F 13/20
[52] U.S. Cl. .................... 604/391; 604/385.1; 604/386; 604/387; 604/389; 604/392
[58] Field of Search .......... 604/358, 385.1, 386–387, 604/389–394, 388; 2/218–221, 235–237, 312, 323, 166; 24/306, 308, 318–319

[56] References Cited

U.S. PATENT DOCUMENTS

| | | |
|---|---|---|
| 1,245,655 | 11/1917 | Allen . |
| 1,494,044 | 5/1924 | Ward et al. . |
| 2,516,951 | 8/1950 | Brink . |
| 2,548,162 | 4/1951 | Karels . |
| 2,564,094 | 8/1951 | Brandl . |
| 2,566,139 | 8/1951 | Ostrovsky et al. . |
| 2,764,158 | 9/1956 | Thornton ............... 604/394 |
| 2,827,052 | 3/1958 | Goodman et al. . |
| 3,081,772 | 3/1963 | Brooks et al. . |
| 3,110,312 | 11/1963 | Wirth . |
| 3,141,461 | 7/1964 | Farris . |
| 3,150,664 | 9/1964 | Noel . |
| 3,196,511 | 7/1965 | Kintner . |
| 3,359,980 | 12/1967 | Rosenblatt . |
| 3,441,024 | 4/1969 | Ralph . |
| 3,441,025 | 4/1969 | Ralph . |
| 3,452,753 | 7/1969 | Sanford . |
| 3,455,303 | 7/1969 | Wilson . |
| 3,460,535 | 8/1969 | Behna . |
| 3,530,859 | 9/1970 | Heimowitz . |
| 3,618,608 | 11/1971 | Brink . |
| 3,653,381 | 4/1972 | Warnken . |
| 3,728,191 | 4/1973 | Wierzba et al. . |
| 3,882,871 | 5/1975 | Taniguchi . |
| 3,955,575 | 5/1976 | Okuda . |
| 4,051,854 | 10/1977 | Aaron . |
| 4,145,763 | 3/1979 | Abrams et al. . |
| 4,171,239 | 10/1979 | Hirsch et al. . |
| 4,241,462 | 12/1980 | Tagawa et al. . |
| 4,259,957 | 4/1981 | Sonenstein et al. . |
| 4,299,223 | 11/1981 | Cronkrite . |
| 4,315,508 | 2/1982 | Bolick . |
| 4,338,938 | 7/1982 | Seavitt . |
| 4,340,563 | 7/1982 | Appel et al. . |
| 4,388,075 | 6/1983 | Mesek et al. . |
| 4,402,690 | 9/1983 | Redfern . |
| 4,405,297 | 9/1983 | Appel et al. . |
| 4,410,327 | 10/1983 | Baggaley . |
| 4,445,242 | 5/1984 | Bowen . |
| 4,475,912 | 10/1984 | Coates . |
| 4,516,975 | 5/1985 | Mitchell . |
| 4,568,342 | 2/1986 | Davis . |
| 4,578,072 | 3/1986 | Lancaster . |
| 4,578,073 | 3/1986 | Dysart et al. . |
| 4,589,878 | 5/1986 | Mitrani . |
| 4,592,118 | 6/1986 | DeWoskin . |
| 4,596,568 | 6/1986 | Flug . |
| 4,597,760 | 7/1986 | Buell . |
| 4,597,761 | 7/1986 | Buell . |
| 4,610,680 | 9/1986 | LaFleur . |

(List continued on next page.)

FOREIGN PATENT DOCUMENTS 672690 7/1960 Canada .

(List continued on next page.)

Primary Examiner—Randall L. Green
Assistant Examiner—P. Zuttarelli
Attorney, Agent, or Firm—Thomas M. Gage

[57] ABSTRACT

An attachment system for securing a garment to a wearer includes attachment pads on front and back waist sections of the garment. A pair of straps extend between the front and back waist sections. In one embodiment, the straps releasably engage adapter elements, which in turn releasably engage some attachment pads. In another embodiment, the straps releasably engage some attachment pads directly and releasably engage buckle-type fasteners, which in turn releasably engage other attachment pads.

23 Claims, 5 Drawing Sheets

U.S. PATENT DOCUMENTS

| | | |
|---|---|---|
| 4,610,682 | 9/1986 | Kopp . |
| 4,615,695 | 10/1986 | Cooper . |
| 4,617,022 | 10/1986 | Pigneul et al. . |
| 4,623,339 | 11/1986 | Ciraldo et al. . |
| 4,630,320 | 12/1986 | Van Gompel . |
| 4,641,381 | 2/1987 | Heran et al. . |
| 4,662,037 | 5/1987 | Provost et al. . |
| 4,663,220 | 5/1987 | Wisneski et al. . |
| 4,670,012 | 6/1987 | Johnson . |
| 4,680,030 | 7/1987 | Coates et al. . |
| 4,681,581 | 7/1987 | Coates . |
| 4,704,117 | 11/1987 | Mitchell . |
| 4,710,414 | 12/1987 | Northrup et al. . |
| 4,728,326 | 3/1988 | Gilles . |
| 4,745,926 | 5/1988 | Hlusko . |
| 4,753,649 | 6/1988 | Pazdernik . |
| 4,761,318 | 8/1988 | Ott et al. . |
| 4,770,917 | 9/1988 | Tochacek et al. . |
| 4,773,906 | 9/1988 | Krushel . |
| 4,776,068 | 10/1988 | Smirlock et al. . |
| 4,781,966 | 11/1988 | Taylor . |
| 4,794,028 | 12/1988 | Fischer . |
| 4,798,603 | 1/1989 | Meyer et al. . |
| 4,801,298 | 1/1989 | Sorenson et al. . |
| 4,834,742 | 5/1989 | Wilson et al. . |
| 4,835,795 | 6/1989 | Lonon . |
| 4,846,815 | 7/1989 | Scripps . |
| 4,847,134 | 7/1989 | Fahrenkrug et al. . |
| 4,854,136 | 8/1989 | Coslovi et al. . |
| 4,869,724 | 9/1989 | Scripps . |
| 4,870,725 | 10/1989 | Dubowik . |
| 4,884,713 | 12/1989 | Handler . |
| 4,886,512 | 12/1989 | Damico et al. . |
| 4,887,338 | 12/1989 | Handler . |
| 4,887,339 | 12/1989 | Bellanger . |
| 4,891,868 | 1/1990 | Watanabe . |
| 4,894,060 | 1/1990 | Nestegard . |
| 4,908,025 | 3/1990 | Ketchum, Jr. . |
| 4,909,802 | 3/1990 | Ahr et al. . |
| 4,909,879 | 3/1990 | Ball . |
| 4,932,950 | 6/1990 | Johnson . |
| 4,936,840 | 6/1990 | Proxmire . |
| 4,937,887 | 7/1990 | Schreiner . |
| 4,938,754 | 7/1990 | Mesek . |
| 4,963,140 | 10/1990 | Robertson et al. . |
| 4,964,860 | 10/1990 | Gipson et al. . |
| 4,973,326 | 11/1990 | Wood et al. . |
| 4,981,480 | 1/1991 | Gaudet et al. . |
| 4,988,346 | 1/1991 | Pfefferkorn . |
| 4,994,054 | 2/1991 | Pigneul et al. . |
| 5,019,073 | 5/1991 | Roessler et al. . |
| 5,021,111 | 6/1991 | Swenson . |
| 5,026,450 | 6/1991 | Cucuzza et al. . |
| 5,032,122 | 7/1991 | Noel et al. . |
| 5,100,399 | 3/1992 | Janson et al. . |
| 5,125,246 | 6/1992 | Shytles . |
| 5,135,522 | 8/1992 | Fahrenkrug et al. . |
| 5,209,743 | 5/1993 | Hardison ............................ 604/358 |

FOREIGN PATENT DOCUMENTS

| | | |
|---|---|---|
| 0013463A1 | 7/1980 | European Pat. Off. . |
| 0120790A1 | 10/1984 | European Pat. Off. . |
| 0233364A2 | 8/1987 | European Pat. Off. . |
| 0276890A2 | 8/1988 | European Pat. Off. . |
| 0276970A2 | 8/1988 | European Pat. Off. . |
| 0278866A1 | 8/1988 | European Pat. Off. . |
| 0287388A2 | 10/1988 | European Pat. Off. . |
| 0319249A1 | 6/1989 | European Pat. Off. . |
| 0321232A1 | 6/1989 | European Pat. Off. . |
| 0321234A1 | 6/1989 | European Pat. Off. . |
| 0330793A1 | 9/1989 | European Pat. Off. . |
| 0345014A3 | 12/1989 | European Pat. Off. . |
| 0374730A2 | 6/1990 | European Pat. Off. . |
| 2335165 | 8/1977 | France . |
| 63-2708 | 1/1988 | Japan . |
| 493819 | 10/1938 | United Kingdom . |
| 1428572 | 3/1976 | United Kingdom . |
| 1430747 | 4/1976 | United Kingdom . |
| 1516287 | 7/1978 | United Kingdom . |
| 2074011A | 10/1981 | United Kingdom . |
| 2144637A | 3/1985 | United Kingdom . |
| 2200530A | 8/1988 | United Kingdom . |
| 2201893A | 9/1988 | United Kingdom . |
| 2233876A | 1/1991 | United Kingdom . |
| 2242612A | 10/1991 | United Kingdom . |
| 2248379A | 4/1992 | United Kingdom . |
| WO85/03205 | 8/1985 | WIPO . |
| WO88/06014 | 8/1988 | WIPO . |
| WO88/07335 | 10/1988 | WIPO . |
| WO91/03220 | 3/1991 | WIPO . |
| WO91/08725 | 6/1991 | WIPO . |
| 9203999 | 3/1992 | WIPO ............................ 604/394 |
| WO92/10957 | 7/1992 | WIPO . |

ADJUSTABLE GARMENT ATTACHMENT SYSTEM

BACKGROUND OF THE INVENTION

The present invention relates generally to the field of garments with attachment systems. More particularly, the invention pertains to an improved adjustable attachment system for maintaining a garment in position on a wearer.

The present invention is intended for use with a wide variety of garments that utilize an attachment system. Such garments may include disposable absorbent articles, bathing suits, athletic supporters, prosthetics, or other personal care or health care garments. With particular reference to disposable absorbent articles, these articles include such things as incontinence garments, disposable diapers, briefs, training pants, or the like. Disposable articles for the absorption and containment of urine and other body exudates are generally unitary, preshaped or prefolded, and are comprised of a fluid pervious bodyside liner, a fluid impervious backing sheet, and an absorbent material disposed between the bodyside liner and the backing sheet. They generally include some type of attachment system for securing the garment to the body of the wearer.

The types of attachment systems used on disposable absorbent articles has varied widely. In some systems, the front and back waist sections are directly attached to one another with a fastener. A number of different fasteners have been employed, such as tape members as disclosed in U.S. Pat. No. 4,753,649 to Pazdernik; complementary hook-and-loop type fasteners as disclosed in U.S. Pat. No. 4,402,690 to Redfern; and snap fasteners as disclosed in U.S. Pat. No. 2,566,139 to Ostrovsky et al. In other attachment systems, the front and back waist sections are connected via a strap or belt. For example, the garment suspension system described in U.S. Pat. No. 4,315,508 to Bolick includes two elastic straps that are provided with buttons or other fastening means. The garment described in U.S. Pat. No. 4,617,022 to Pigneul et al. includes a removable belt that may be attached to the garment with hook-and-loop type fasteners.

In order to effectively absorb and contain urine and other body exudates, disposable absorbent articles must properly fit the body of the wearer. Due to cost constraints, garment manufacturers have not produced absorbent articles in an infinite number of sizes. Instead, garment manufactures have designed absorbent articles that are adjustable. In existing disposable absorbent garments, adjustability has been accomplished by providing a range of locations over which the front and back waist sections can be oriented relative to one another. In U.S. Pat. No. 4,728,326 to Gilles, for instance, a diaper is disclosed which has straps that include hook members at the ends of the straps. The hook members attach to a loop member, which extends across the entire back waist section of the diaper. Similarly, U.S. Pat. No. 4,801,298 to Sorenson et al. utilizes a hook-and-loop fastener with a loop strip extending across the front of the diaper, and U.S. Pat. No. 4,315,508 to Bolick discloses elastic straps with buttons that may be secured within any one of a series of button holes. See also U.S. Pat. Nos. 2,516,951 to Brink; 2,564,094 to Brandl; 2,566,139 to Ostrovsky et al.

One significant drawback associated with the foregoing type of adjustable garments is that the proper adjustment is not maintained if the attachment system is released and subsequently refastened. This drawback is particularly significant with regard to attachment systems, such as straps or belts, that are intended to be used repeatedly. By way of illustration, incontinence products are presently distributed in packages containing multiple, identical absorbent shells along with a lesser number of attachment straps. Thus, a single attachment strap is intended to be used with a number of absorbent shells. Present attachment systems provide no mechanism whereby an attachment strap may be adjusted for one absorbent shell and transferred to another, identical shell while maintaining the proper adjustment for the wearer.

Another drawback associated with present attachment systems arises from the fact that reusable attachment straps are subject to a large number of attach-detach cycles. For hook-and-loop attachment systems, this has meant that the less durable loop material could not be used on the reusable strap, or that the strap would tend to wear rapidly and fail during repeated use.

SUMMARY OF THE INVENTION

In response to the discussed drawbacks and problems encountered in the past, a new garment with an attachment system has been discovered. A garment according to this invention includes a garment shell having a first waist section and a second waist section. The garment also includes at least one strap member and an adapter element. The adapter element has a first surface that is releasably engageable with the first waist section, and an opposite second surface that is releasably engageable with the strap member. This aspect of the invention provides a garment with an attachment system that is readily adjustable to achieve the proper length and fit for the wearer.

In another aspect of the invention, the force required to release the first surface of the adapter element from the first waist section is less than the force required to release the second surface of the adapter element from the strap member. This aspect causes the adapter element to remain attached to the strap member when the strap is separated from the garment shell. Consequently, when the strap member and the attached adapter element are again attached to the shell, or attached to a similar shell, the strap member will already be adjusted to the proper length.

In still another aspect of this invention, a garment includes a garment shell having a first waist section and a second waist section. An attachment pad is attached to the first waist section, and a buckle-type fastener is releasably engageable with the attachment pad. The garment includes at least one strap member having a first end and a second end. A portion of the strap member adjacent the first end is releasably attached to the buckle, and a portion of the strap member adjacent the second end is releasably attached to the second waist section. This aspect of the invention provides another form of adjustable attachment system. The position where the first end of the strap member is attached to the buckle determines the effective length of the strap member. The wearer may select the desired effective length to obtain a proper fit.

In still another aspect, the buckle defines a slot, and the first end of the strap member is sized to fit in the slot. The buckle includes a primary grouping of hooks that are releasably engageable with the attachment pad, and may include a secondary grouping of hooks for releasably attaching the first end of the strap to the buckle.

As can be seen from the foregoing comments, it is an object of the present invention to provide a garment and an attachment system that properly secures the garment about the body of a wearer.

It is another object of the invention to provide a garment and an attachment system, where the attachment system is adjustable so that a particular size garment may be modified to properly fit the wearer.

It is another object of the invention to provide an attachment system that can be adjusted to properly fit the wearer, and can subsequently be detached and refastened without having to again adjust the attachment system to obtain the proper fit.

It is still another object of the invention to provide a garment attachment system incorporating components that can be used repeatedly, thereby increasing the useful life of the attachment system.

It is a further object of the invention to provide a disposable absorbent garment and an attachment system therefor that can be manufactured in an efficient manner.

The foregoing and other objects, features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DETAILED DESCRIPTION OF THE PREFERRED EMBODIMENTS

Figure 1:
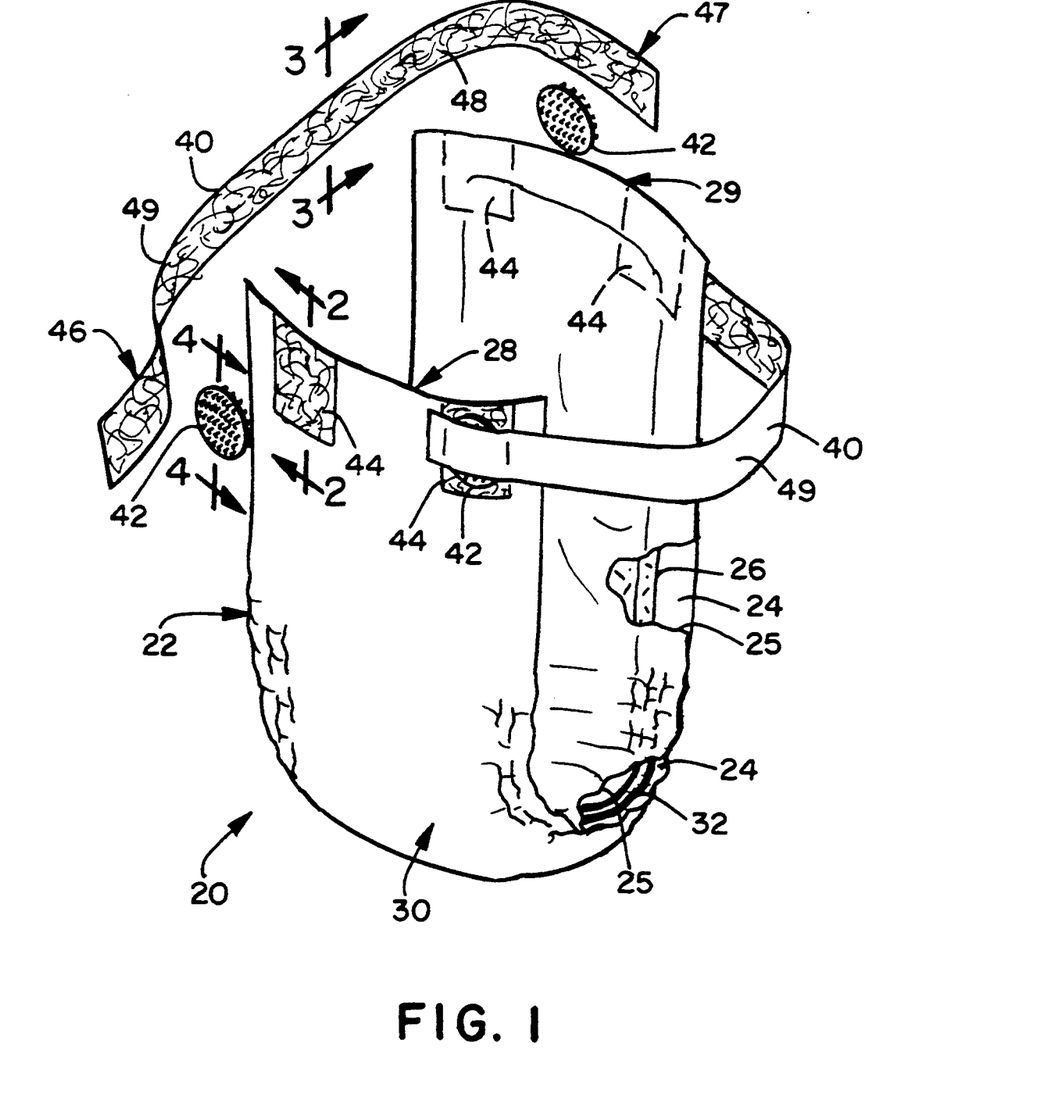
FIG. 1 is a partially-exploded perspective view of a disposable absorbent garment according to the present invention, with portions broken away for the purposes of illustration.

With reference to FIG. 1, a disposable absorbent garment 20 formed according to the present invention is shown for purposes of illustration as an incontinence product for adults. The invention may also be embodied in other types of garments, such as bathing suits, athletic supporters, prosthetics, or other personal care or health care garments.

The disposable absorbent garment 20 generally includes a garment shell 22 that is adapted to be used in conjunction with an attachment system. As shown, the shell 22 includes a substantially liquid impermeable backing sheet 24, a substantially liquid permeable bodyside liner 25, and an absorbent core 26 positioned between the backing sheet and the bodyside liner. The backing sheet 24 and bodyside liner 25 are preferably longer and wider than the absorbent core 26, so that the peripheries of the backing sheet and bodyside liner form margins which may be sealed together using ultrasonic bonds, adhesives, or other suitable means. The absorbent core 26 may be attached to the backing sheet 24 and/or the bodyside liner 25 using ultrasonic bonds, adhesives, or other suitable means. The garment 20 may also include additional components to assist in the acquisition, distribution and storage of waste material. For example, the garment 20 may include a transport layer, such as described in U.S. Pat. No. 4,798,603 to Meyer et al., which is incorporated herein by reference to the extent that it is consistent herewith.

The garment shell 22 is generally rectangular with a front waist section 28 and an opposite back waist section 29. A crotch section 30 is located intermediate the front and back waist sections 28 and 29. Of course, the shell may optionally be T-shaped, I-shaped, hourglass-shaped, or irregularly-shaped. The shell 22 may include elastic strands or ribbons 32 longitudinally orientated along each side margin of the garment 20 and attached to the backing sheet 24, the liner 25, or both. The elastic strands 32 are located in the crotch section 30 and extend toward or into the front and back waist sections 28 and 29. The elastic strands 32 may assist in holding the shell 22 against the body of the wearer or forming seals or gaskets about the leg of the wearer.

The attachment system in this embodiment of the invention includes a pair of strap members 40, four adapter elements 42, and four attachment pads 44. Two of the attachment pads 44 are located in the front waist section 28, separated from one another and positioned adjacent the front longitudinal end of the garment 20. The other two attachment pads 44 are located in a comparable position in the back waist section 29 of the garment 20. Each attachment pad 44 is attached by ultrasonic bonds, adhesives, or other suitable means, to the surface of the backing sheet 24 that is remote from the bodyside liner 25.

Figures 2, 4:
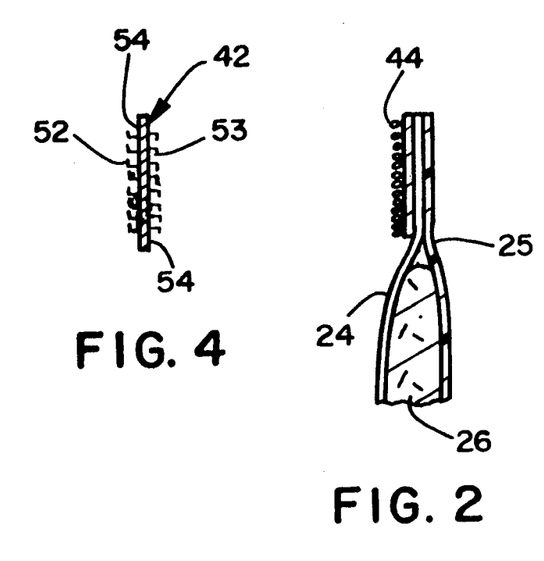
FIG. 2 is an enlarged view in section taken generally from the plane of the line 2—2 in FIG. 1.
FIG. 4 is an enlarged view in section taken generally from the plane of the line 4—4 in FIG. 1 and showing an adapter element.

As shown most clearly in FIG. 2, the attachment pads 44 are preferably on one surface formed of a loop fabric material, which comprises the loop component of a hook-and-loop fastening system. The loop fabric material can comprise a material manufactured to have a raised loop construction, stabilized through napping and thermosetting so that the individual loops are erect from the fabric base. The loop material may be formed of any suitable material, such as acrylic, nylon or polyester, and may be formed by methods such as warp knitting, stitch bonding or needle punching. The attachment pads 44 can also be any suitable material having non-woven loops thereon.

The attachment pads 44 may, by way of example, have a two bar warp knit construction, with from 21 to 41 courses per inch (ca. 8–16 per cm.) and from 26 to 46 wales per inch (ca. 10–18 per cm.), of polyester yarn. In particular, about 15-35 percent of the yarns may be composed of yarn having about 1-30 individual filaments therein and having a yarn denier within the range of about 15–30 d (denier). In addition, about 65–85 percent of the yarns may be composed of yarn having about 1–30 individual filaments therein and having a yarn denier within the range of about 20–55 d. Also, the loops may particularly be formed with a loop height from about 2 to about 2.5 millimeters. The caliper may be from about 0.010 to about 0.040 inch (ca. 0.25–1 mm.) and the basis weight may be from about 1.0 to about 3.0 ounces per square yard (ca. 34–102 grams per square meter). One particular material which has been found suitable for the attachment pads 44 is identified as No. 19902 and is available from Guilford Mills of Greensboro, N.C.

The attachment pads 44 are attached to the backing sheet 24 so that the loops of the loop material extend outwardly from the backing sheet. The geometric shape of the attachment pads 44 may take any form, such as square, rectangular, irregular, oval, round, etc. The attachment pads 44 may be aligned with the longitudinal axis of the garment 20, or attached at an angle thereto as disclosed in commonly assigned U.S. patent application Serial No. unassigned, filed on the same date as the instant application, by D. A. Kuen et al. for a "Garment Attachment System". The size of the attachment pads 44 should be sufficient to be readily detectible by sight and touch, and adequate to receive an adapter element 42. It has been found, for example, that rectangular pads of approximately 1.25 inches by 3.38 inches (ca. 3 by 9 cm.) are desirable in the front waist section 28 and rectangular pads of approximately 1.5 inches by 2 inches (ca. 4 by 5 cm.) are desirable in the back waist section 29.

Figure 3:
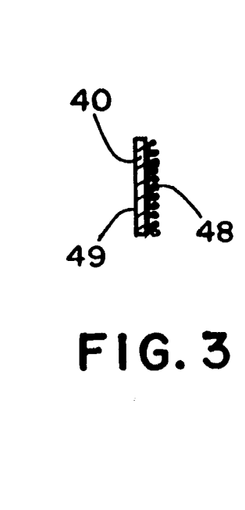
FIG. 3 is an enlarged view in section taken generally from the plane of the line 3—3 in FIG. 1.

The strap members 40, which are illustrated in FIGS. 1 and 3, are each generally rectangular strips of material having opposite forward and rearward end portions 46 and 47. The strap members 40 are preferably formed of an elastic material, which is capable of stretching to approximately 2.8 to 3 times its relaxed length. The strap members 40 preferably have a length from about 6 inches to about 16 inches (ca. 15–41 cm.), and a width from about 0.5 inch to about 1.5 inches (ca. 1–4 cm.). For example, each strap member 40 may be 11 inches (ca. 28 cm.) long and 1 inch (ca. 2.5 cm.) wide. The cut ends of the strap members 40 may be bonded by ultrasonics, adhesives or other suitable means to prevent raveling.

The strap members 40 have a looped face 48 and an opposite face 49. The inwardly-directed looped face 48 of each strap member 40 is formed of a loop material, such as by attaching a loop material to an elastic strap material. The loop material may be attached only at the forward and rearward end portions 46 and 47, or along the entire length of the strap member 40. More preferably, the looped face 48 is separately stitched or permanently and continuously formed lock-stitched into one side of a woven or knit elastic material as it is woven or knitted. One particular material which has been found suitable as a strap member 40 is a knit material identified as S-284 and manufactured by Shelby Elastics, Incorporated of Shelby, N.C. A knitted elastic lock pile fabric is disclosed in U.S. Pat. No. 5,125,246 to Shytles.

Figure 5:
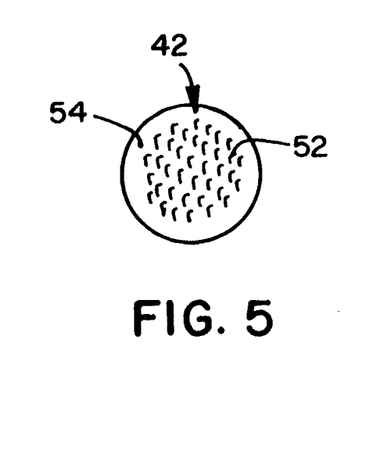
FIG. 5 is a plan view of the adapter element shown in FIG. 4.

With additional reference to FIGS. 4 and 5, each of the four adapter elements 42 has a first surface 52 and an opposite second surface 53. Each surface 52 and 53 is formed of outwardly-extending hook members, which comprise the hook component of the hook-and-loop system. A perimeter portion 54 of each of the surfaces 52 and 53, radially outward from the hook members, is preferably generally flat and free of hook members. These flat perimeter portions 54 provide a convenient place at which to grasp the adapter elements 42.

The adapter elements 42 can be constructed by attaching two single-sided hook materials together with adhesives or other suitable means in back-to-back relationship. The two single-sided hook materials can be attached, for instance, on opposite sides of a plastic film or other suitable material. Alternately, a single-sided hook material can be folded and bonded onto itself to form the adapter elements 42. Still alternately, the adapter elements 42 can be integrally molded or extruded with the hook members on each of the first and second surfaces 52 and 53. Suitable hook material may be molded or extruded of nylon, polypropylene or another suitable material. Desirable stiffness levels of the hook material may be obtained from polymeric materials having a flexural modulus of about 70,000–120,000 pounds per square inch (ca. $4.83 \times 10^8 - 8.27 \times 10^8$ nt/m$^2$) and a Shore hardness value within the range of about D-40 to D-80, such as D-61. One suitable single-sided hook material is available from Velcro Industries B.V., Amsterdam, Netherlands or affiliates thereof, is identified as HTH 708, and preferably includes bidirectional hooks.

The shape, density and polymer composition of the hook members on the first and second surfaces 52 and 53 of the adapter elements 42 are preferably although not necessarily the same. The density of the hook members may be selected to provide desirable peel and shear force resistance values as hereinafter described. The density may, for instance, be more than 50 hooks per square inch (ca. 8 per square cm.), and more particularly within the range of about 440 to about 1040 hooks per square inch (ca. 68–161 per square cm.), such as about 740 hooks per square inch (ca. 115 per square cm.). The row density may be within the range of about 20 to about 60 rows per linear inch of width (ca. 8–24 per linear cm.), such as about 40 rows per linear inch of width (ca. 16 per linear cm.). The hook members may be hook-shaped, mushroom-shaped, arrow-shaped or any other desired shape.

Most preferably, the hook members on the first and second surfaces 52 and 53 are identically formed. Additionally, it is preferred that the hook members of the adapter elements 42 attach more securely to the loop material of the strap members 40 than to the loop material of the attachment pads 44. This may be accomplished in a variety of ways known in the art, such as by forming the looped face 48 of the strap members 40 with a relatively stronger loop filament, a higher standing or more easily engageable loop shape, a more dense arrangement of loops, or any combination of these or similar characteristics. By way of illustration, the looped face 48 may have a loop density that is greater than the loop density of the attachment pads 44. The looped face 48, for instance, may have a loop density greater than about 80 loops per square inch in the unstretched state, or more preferably about 420 loops per square inch in the unstretched state. Alternately or in combination therewith, the loop height on the looped face 48 may be greater than on the attachment pads 44, such as from about 0.25 to about 5 millimeters, more particularly from about 2 to about 2.5 millimeters.

The adapter elements 42 as illustrated in the drawings are round in shape. The adapter elements 42 may, however, be any desired shape, such as square, rectangular, irregular, oval, etc. Additionally, the shape of the adapter elements 42 may be, but need not be, the same as the shape of the attachment pads 44. The adapter elements 44 may, for example, be rectangular or square with length and width dimensions of from about 0.25 inch to about 2 inches (ca. 0.5–5 cm.), or be circular with a diameter of from about 0.25 inch to about 2 inches (ca. 0.5–5 cm.). Most preferably, the adapter elements 42 are shaped such that they may be easily grasped and removed from the strap members 40. In this regard, the flat perimeter portions 54 of the adapter elements 42 act as finger tabs for easily handling the adapter elements.

The garment shell 22 is positioned on the body of the wearer and secured in position using the attachment system. The four adapter elements 42 are initially attached to the four attachment pads 44. It does not matter which of the first or second faces 52 or 53 of the adapter elements 42 are attached to the attachment pads 44, if the faces are substantially identical, as is preferred. The wearer then attaches the looped face 48 of a strap member 40, near the rearward end portion 47, to an adapter element 42 attached to the back waist section 29 of the shell 22. The second strap member 40 is then attached to the other attachment pad 44 on the back waist section 29 in a similar manner.

The wearer then stretches or relaxes the strap members 40 to obtain the desired effective length to provide the proper fit. The wearer next attaches the looped faces 48 of the strap members 40, near the forward end portions 46, to the corresponding adapter elements 42 attached to the front waist section 28. The effective length of a strap member 40 is considered to be the portion of the strap member between the two locations where adapter elements 42 are attached thereto, when the strap member is unstretched and attached to the garment shell 22 in the manner described. In this way, the hook members on one surface 52 or 53 of an adapter element 42 releasably secure the adapter element to the loop material on a strap member 40, and the hook members on the other surface 52 or 53 of the adapter element releasably secure the adapter element to the loop material on an attachment pad 44.

Once the garment 20 has been properly adjusted and secured as described, the strap members 40 can be repeatedly detached and re-attached to the shell 22 without the wearer having to re-adjust the strap members to obtain the proper effective length. The wearer can remove a strap member 40 by pulling on a portion of the strap near an adapter element 42. The strap member 40 will separate from the attachment pad 44, and when the hook members of the adapter elements 42 are designed to attach more securely to the loop material of the strap members 40 than to the loop material of the attachment pads 44 as previously described, the adapter element 42 will remain attached to the strap member. More particularly, the adapter elements 42 will separate more easily from the attachment pads 44 than from the strap members 40, because the peel or shear force required to remove an adapter element 42 from a strap member 40 is greater than that required to remove an adapter element from an attachment pad 44.

The "shear force" as referenced herein is determined according to ASTM Designation: D3654-82, "Standard Test Method for Holding Power of Pressure-Sensitive Tapes", which is incorporated herein by reference, and subject to the following modifications: In relation to the test, the closure is placed under an increasing load. The system being tested is a hook and loop closure system. (See 1. Scope). The apparatus should include an "INSTRON" or equivalent continuous rate of extension (CRE) tensile tester. (See 3. Apparatus). In carrying out the procedure (see 6. Procedure), test direction of the materials should be noted. The test materials are rolled five cycles (1 sq. in.), where one cycle equals once in each direction. The hook material is clamped into the upper jaw and the loop material clamped into the lower jaw of the Instron tensile tester. The engaged system (hook and loop) is pulled until failure. In doing the calculations (See 10. Calculations), the peak load is determined and recorded in grams.

The "peel force" is determined according to ASTM Designation: D1876-72, "Standard Test Methods for Peel Resistance of Adhesives (T-Peel Test)", which is incorporated herein by reference, and subject to the following modifications: 4.1 No test panels are used; hook and loop materials are directly engaged and are not mounted on any other substrate unless specified. Test direction of the materials should be noted. No panels are used. The engaged test materials are rolled five cycles; where one cycle equals once in each direction. The hook material is clamped into the upper jaw and the loop material is clamped into the lower jaw.

To adequately attach the strap members 40, the adapter elements 42 secure to the attachment pads 44 with a total peel resistance of at least about 150 gm., and more preferably at least about 400 gm. The adapter elements 42 secure to the attachment pads 44 with a total shear force resistance of at least about 750 gm., and more preferably at least about 1000 gm. The peel and shear force resistance values for the engagement of the adapter elements 42 to the strap members 40 are preferably greater than those for engagement of the adapter elements to the attachment pads. It should be readily recognized that a suitable fastening system will include a selected balance between the properties of total peel resistance and total shear force resistance. For example, a system with the lower values of peel resistance could be more suitable if the system also exhibited a higher total shear force resistance.

For purposes of the present description, the total peel resistance value corresponds to the peel force determined in accordance with ASTM D1876-72 multiplied by the transverse width of engagement between the hook material and the loop material employed in the particular fastening system. Similarly, the total shear force resistance value corresponds to the shear stress determined in accordance with ASTM D3654-82 multiplied by the area of engagement between the hook material and loop material of the fastening system.

The wearer can re-attach the strap members 40 to the shell 22 by pressing the adapter elements 42, which remain attached to the strap members, into engagement with the attachment pads 44. Thus, the incorporation of hook-and-loop fasteners allows the strap members 40 to be repeatedly attached and detached, either to the same garment shell 22 or to the shell of a different garment. Advantageously, the wearer will know that the strap members 40 will be adjusted to the proper effective length upon reattachment, because two of the adapter elements 42 remain attached to each of the strap members.

The present attachment system also allows the wearer to change the effective length of the strap members 40. For example, when one end portion 46 or 47 of a strap member 40 is detached from its associated attachment pad 44, the wearer need only remove the adapter element 42 that is fastened to that end portion, and reattach it closer to or further from the end portion. Changing the placement of the adapter elements 42 on a strap member 40 modifiers the effective length of the strap member. Thus, the wearer can modify the effective length as circumstances dictate, in order obtain a proper fitting garment 20.

It will be appreciated that the majority of the engaging and releasing that occurs between the hook and the loop components of the present system takes place between the adapter elements 42 and the attachment pads 44. This reduces wear on the loop members of the strap member 40, thereby increasing the useful life of the strap members. Generally, hook members, such as those on the adapter elements 42, are more durable than loop members, such as those forming parts of the strap members 40 and the attachment pads 44. Relatedly, the relatively soft looped faces 48 of the strap members 40 of the attachment system are positioned toward the body of the wearer, to provide a comfortable fit and provide air circulation between the strap member and the wearer's skin.

The present invention contemplates numerous modifications to the absorbent garment 20, such as providing only one adapter element 42 for use with each strap member 40. In this case, the rearward end portion 47 of each strap member could be fixedly attached (See FIG. 6) to the back waist section 29. Still optionally, the rearward end portion of each strap member could include a portion of hook material, or the attachment pads 44 located in the back waist section could be formed of a hook material rather than a loop material. The present invention also contemplates employing a relatively larger, single attachment pad (not shown), to replace two pads on either waist section 28 or 29, or to replace all four pads. In this latter case, it can be seen that the attachment pad could be the same size as the backing sheet, or be formed of liquid impermeable material to function as the backing sheet itself. Likewise, the present invention contemplates interchanging the position or placement of the hook members and the loop members on their particular surfaces.

Figure 6:
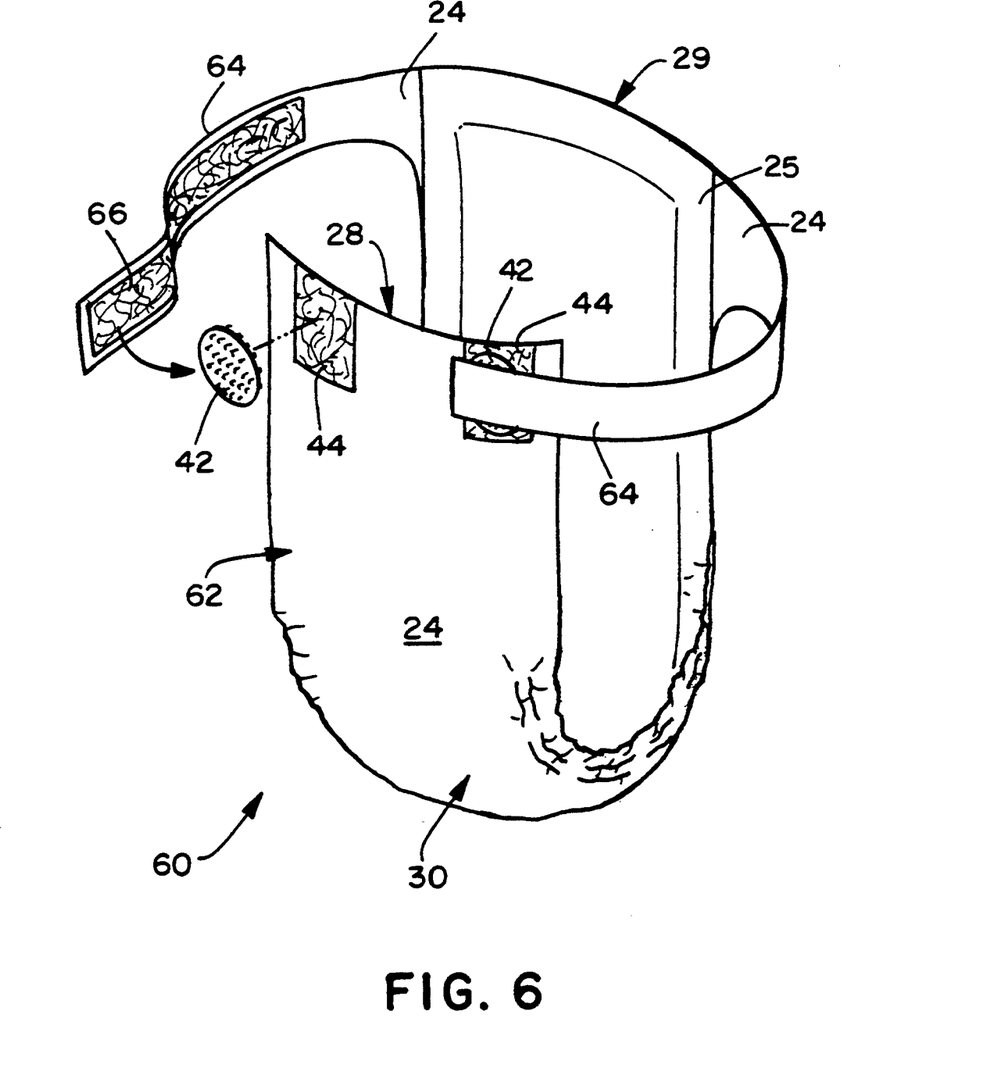
FIG. 6 is a partially-exploded perspective view of a second embodiment of the invention.

A second embodiment of the present invention is illustrated in FIG. 6 as another disposable absorbent garment 60. Components similar to those previously described have been given the same reference numeral. The garment 60 includes a shell 62 comprising a backing sheet 24, a bodyside liner 25, and an absorbent core 26 (not shown) positioned between the backing sheet and the bodyside liner. The shell 62 is formed with a front waist section 28, an opposite back waist section 29, and a crotch section 30. The longitudinal sides of the crotch section 30 may include elastic strands 32 (not shown) between the bodyside liner 25 and the backing sheet 24 to form seals or gaskets about the leg of the wearer.

Strap members 64 of the shell 62 project transversely outward from the back waist section 29 adjacent the back longitudinal end of the garment 60. The strap members 64 may be formed from or attached to the backing sheet 24. Loop patches 66 formed of a loop material are attached by adhesives, ultrasonic bonds or other suitable means to each strap member 64. The loop material on the loop patches 66 is desirably the same material as previously described in relation to the looped face 48 of the strap members 40 (FIGS. 1 and 3).

As an alternative (not shown), the strap members could be formed exclusively of the loop patch material.

Two attachment pads 44 are attached to the backing sheet 24 in the front waist section 28 of the shell 22. The attachment pads 44 are separated from one another and positioned adjacent the front longitudinal end of the garment 60. Optionally, a single attachment pad (not shown) could extend transversely across the front waist section 28.

The attachment system for the garment 60 also includes a pair of adapter elements 42. The adapter elements 42 have opposite, preferably identical surfaces 52 and 53 including outwardly-extending hook members and flat perimeter portions 54 (see FIGS. 4 and 5). The hook members of the adapter elements 42 are releasably fastenable to the loop material of the loop patches 66 and the loop material of the attachment pads 44.

The garment 60 can be secured to the body of a wearer by attaching the loop patches 66 of the strap members 64 to the adapter elements 42, and attaching the adapter elements to the attachment pads 44. A strap member 64 can be detached from the front waist section 28 by pulling on the strap member near its corresponding adapter element 42. The adapter element 42 will detach from its corresponding attachment pad 44 and remain attached to its corresponding loop patch 66, if the hook members of the adapter element are designed to attach more securely to the loop patch than to the attachment pad. The strap member 64 can be reattached in the same position as it was previously attached, by pressing the adapter element 42 onto the attachment pad 44. Alternately, the fit of the garment 60 can be modified by moving the adapter elements 42 further from or closer to the end of the loop patches 66.

Figure 7:
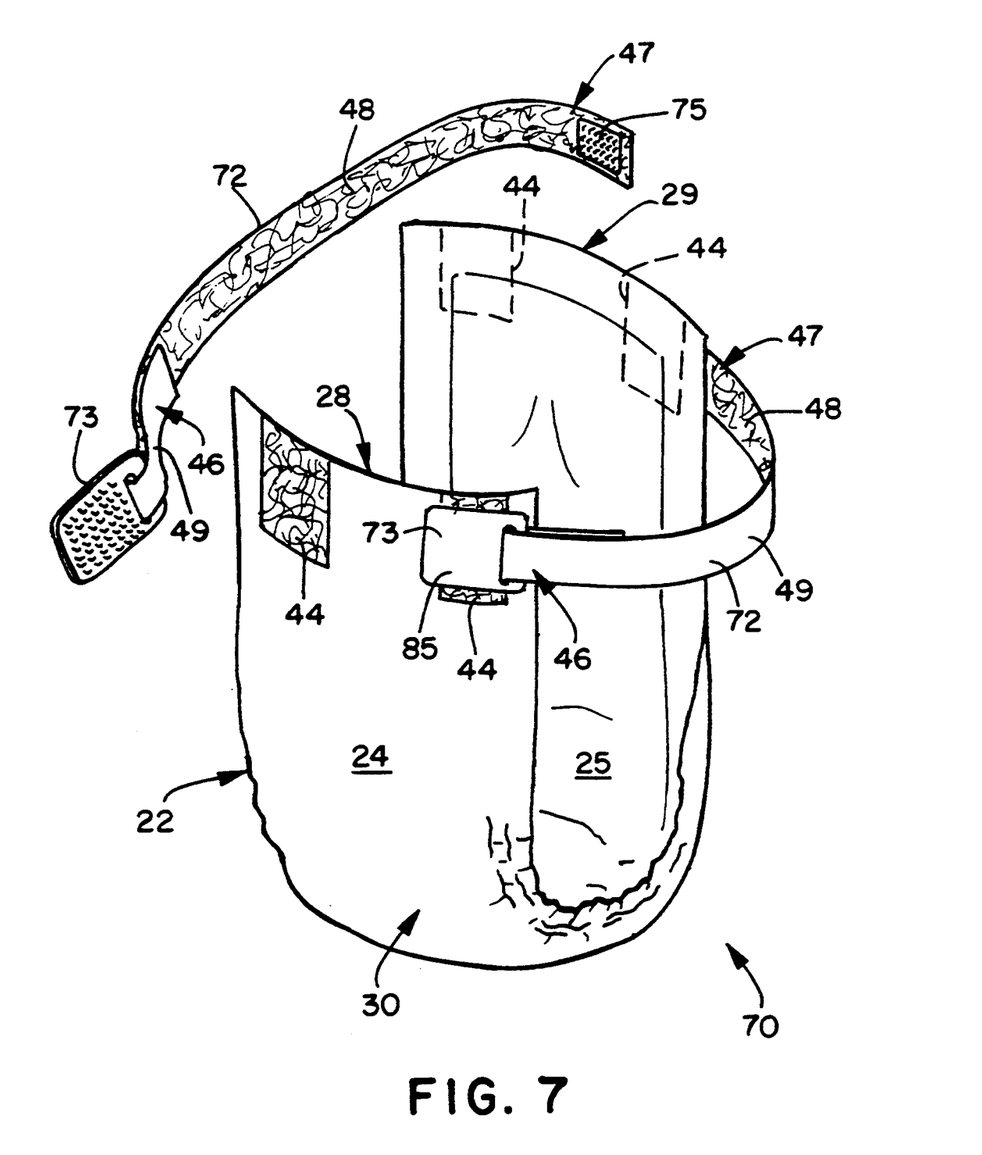
FIG. 7 is a perspective view of a third embodiment of the invention.

A third embodiment of the invention is illustrated by the garment 70 in FIG. 7. The garment 70 includes a shell 22 comprising a backing sheet 24, a bodyside liner 25, and an absorbent core 26 (not shown) positioned between the backing sheet and the bodyside liner. The shell 22 is formed with a front waist section 28, an opposite back waist section 29, and a crotch section 30. As with other embodiments, the sides of the crotch section 30 may include elastic strands 32 (not shown) to form seals or gaskets about the leg of the wearer.

The attachment system for the garment 70 includes four attachment pads 44, two strap members 72, and two buckle-type fasteners 73. Like the embodiment of FIG. 1, two attachment pads 44 are located in the front waist section 28 and two attachment pads 44 are located in the back waist section 29. The attachment pads 44 in both the front and the back waist sections are separated from one another and positioned adjacent a longitudinal end of the garment 70. Optionally, one or two larger attachment pads (not shown) could be used in place of the four pads shown. Each attachment pad 44 is attached by ultrasonic bonds, adhesives, or other suitable means, to the surface of the backing sheet 24 that is remote from the bodyside liner 25. As a result, the loops of the attachment pad loop material extend outwardly from the backing sheet 24. The size of the attachment pads 44 is desirably larger than the size of the buckles 73, and may for example be about 1.25 inch by 2 inches (ca. 3 by 5 cm.).

Figure 9:
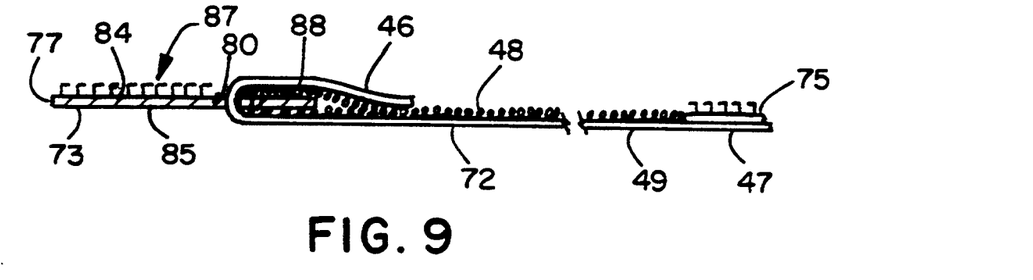
FIG. 9 is an enlarged view in section of portions of the attachment system shown in FIG. 7.

The strap members 72, shown in FIGS. 7 and 9, are generally rectangular strips of material that are preferably capable of stretching to approximately 2.8 to 3 times their relaxed length. Each strap member 72 has opposite forward and rearward end portions 46 and 47, and is preferably from about 6 inches to about 16 inches (ca. 15–41 cm.) in length, and from about 0.5 inch to about 1.5 inches (ca. 1–4 cm.) in width. For example, each strap member 72 may be 11 inches (ca. 28 cm.) long and 1 inch (ca. 2.5 cm.) wide.

The strap members 72 have a looped face 48 and an opposite face 49. The looped face 48 of each strap member 72 is formed of a loop material. For example, the looped face 48 may be formed as a loop material and attached to the elastic strap material, or more preferably and as represented in the drawings, the looped face 48 may be separately stitched or integrally formed lock-stitched into one side of a woven or knitted elastic material. The loop material on the looped face 48 may have a loop density of about 80 loops per square inch in the unstretched state, particularly about 420 loops per square inch in the unstretched state. The loop height on the looped face 48 is from about 0.25 to about 5 millimeters, more particularly from about 2 to about 2.5 millimeters. One particular material which has been found suitable as a strap member 72 is identified as S-284 and is manufactured by Shelby Elastics, Incorporated of Shelby, N.C.

Each strap member 72 includes a hook patch 75, which comprises a single-sided hook material. The hook patches 75 (only one shown in FIG. 6) form a hook component of the hook-and-loop attachment system. The hook patches 75 may be rectangular in shape, and about 0.875 inch by about 1.125 inches (ca. 2.2 by 2.9 cm.), for example. Each hook patch 75 is attached by ultrasonic bonds, adhesives, stitches or other suitable means, to the looped face 48 of the strap member 72, adjacent the rearward end portion 47. Particularly, the hook patches 75 may be attached approximately 0.25 inch (ca. 0.6 cm.) from the rearward ends of the strap members 72, with the hooks extending outwardly from the strap member. Optionally, the hook patches 75 may be attached so as to project beyond the rearward ends of the strap members 72 (not shown).

The hook patches 75 may be formed of any suitable material, such as nylon or polypropylene. Desirably, the hook patches 75 contain a uni-directional hook material, with the machine direction of the hooks aligned with the longitudinal axis of the strap members 72, and the hooks facing toward the forward end portion 46 of the strap member. One suitable material for the hook patches 75 is available from Velcro Industries B.V., Amsterdam, Netherlands or affiliates thereof, and is identified as HTH 708 with No. 15 uni-directional hook pattern.

Figure 8:
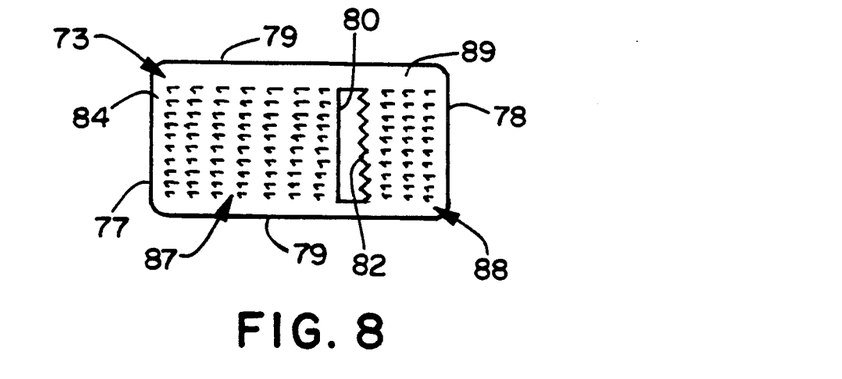
FIG. 8 is an enlarged plan view of a fastener element of the attachment system shown in FIG. 7.

The buckles 73 of the garment attachment system also form a hook component of the hook-and-loop attachment system. As best shown in FIG. 8, the buckles 73 are preferably rectangular in shape with first and second ends 77 and 78, and sides 79 extending between the ends. A generally rectangular-shaped slot 80 is formed in each buckle 73. The slot 80 is preferably off-set toward the second end 78, and positioned so that the long dimension of the slot extends toward the sides 79 of the buckle 73. The long dimension of the slot 80 that is located closest to the second end 78 may be formed with a toothed pattern 82.

The slot 80 is sized to allow a strap member 72 to pass through the slot. Specifically, the long dimension of the slot 80 is preferably longer than the width of the strap members 72. The slot 80 may, for instance, be about 1⅛ inches by at least about 3/16 inches (ca. 2.9 by 0.5 cm.).

The overall dimensions of the buckles 73 may be about 2 inches by about 1⅜ inches (ca. 5.1 by 3.5 cm.).

The buckles 73 are formed with a first surface 84 and an opposite second surface 85, as seen by comparing the two buckles in FIG. 7 and with reference to FIGS. 8 and 9. Primary and secondary groupings 87 and 88 of hooks extend outwardly from the first surface 84. The primary grouping 87 is positioned generally between the slot 80 and the first end 77, while the secondary grouping 88 is positioned generally between the slot and the second end 78. The primary and secondary groupings 87 and 88 preferably extend toward the sides 79 to approximately the same extent as the slot 80. Desirably although not necessarily, the perimeter 89 (see FIG. 8) of the first surface 84 is free of hooks, thereby providing a convenient location to grasp the buckle 73. The second surface 85 is generally smooth and also free of hooks.

The buckles 73 may be formed of any suitable material such as polypropylene, although relatively strong materials such as nylon are preferred. Desirably, the hooks on the first surface 84 are uni-directional and oriented with the machine direction of the hooks aligned with the longitudinal axis of the buckle 73. The hooks should face toward the second end 78 of the buckle 73. The buckles 73 may be formed by laminating a single-sided hook material to a base material, or integrally molding the hook and base portions. One suitable single-sided hook material for use in constructing laminated buckles 73 is available from Velcro Industries B.V., Amsterdam, Netherlands or affiliates thereof, and is identified as HTH 708 with No. 15 uni-directional hook pattern.

The shape and density of the hook members on the buckles 73 may be selected to provide a secure, releasable connection to the attachment pads 44. The density of the hook members, for example, may be greater than 50 hooks per square inch (ca. 8 per square cm.), and more particularly within the range of about 440 to about 1040 hooks per square inch (ca. 68–161 per square cm.), such as about 740 hooks per square inch (ca. 115 per square cm.), with a row density within the range of about 20 to about 60 rows per linear inch of width (ca. 8–24 per linear cm.), such as about 40 rows per linear inch of width (ca. 16 per linear cm.). The hook members may be hook-shaped, mushroom-shaped, arrow-shaped or any other desired shape to provide the secure, releasable connection.

In use, the garment shell 22 is positioned on the body of the wearer. Next, the hook patches 75 on each strap member 72 are releasably secured to the attachment pads 44 on the back waist section 29 of the shell 22. As can be appreciated, the hook patches 75 and the back attachment pads 44 function together to releasably attach the rearward end portions 47 of the strap members 72 to the back waist section 29.

Each forward end portion 46 of the strap members 72 is inserted through the slot 80 in a buckle 73. The insertion is performed so that each forward end 46 enters the slot 80 on the second surface 85 side, and exits on the first surface 84 side. Each strap member 72 is folded back against the toothed pattern 82 and onto itself, as suggested in FIG. 9. In this way, the looped face 48 of each strap member 72 releasably engages the secondary grouping 88 of hooks. This hook-and-loop engagement and the contact with the toothed pattern 82 are effective to releasably attach a portion of each strap member 72 near the forward end 46 to a buckle 73.

To finish securing the garment 70 on the wearer, the primary grouping 87 of hooks on each buckle 73 is releasably secured to the loops on the corresponding attachment pad 44 on the front waist section 28. The position of the primary grouping 87 on the attachment pad 44 may be changed to make minor adjustments to the tension of the strap member. Moving the primary grouping 87 in this manner, however, does not change the effective length of a strap member. The effective length is considered to be the distance between the primary grouping of hooks and the hook patch 75, with the strap member 72 in an unstretched state.

The attachment system may be quickly and easily removed by pulling on the buckles 73 to release them from the front attachment pads 44, or by pulling on the rearward end portions 47 to release the hook patches 75 from the back attachment pads 44. The smooth perimeter portions 89 of the buckles 73 provide a convenient location at which to grasp the buckles.

As with the other embodiments, the wearer can modify the effective length of a strap member 72 as circumstances dictate in order to obtain a proper fitting garment 70. This is accomplished by releasing the looped face 48 from the secondary grouping 88 of hooks, and either increasing or decreasing the amount of the strap member 72 that extends through the slot 80. When the desired length is obtained, the looped face 48 is again secured to the secondary grouping 88 of hooks.

Figure 10:
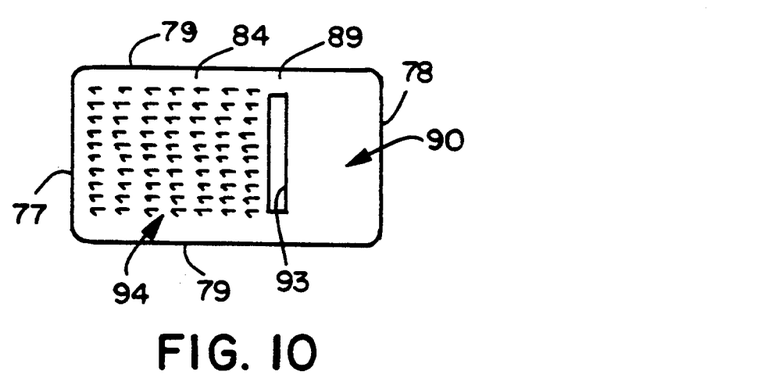
FIG. 10 is an enlarged plan view similar to FIG. 8, but showing an alternate type of fastener element.
Figure 11:
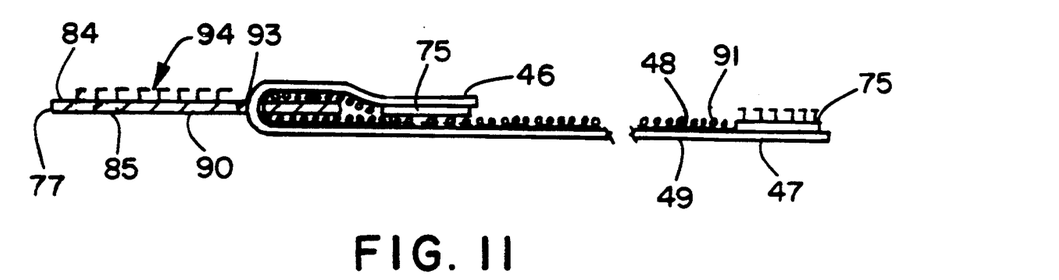
FIG. 11 is an enlarged view in section similar to FIG. 9, but showing an attachment system incorporating the fastener element of FIG. 10.

In FIGS. 10 and 11, an alternate attachment system is shown for use with the garment shell 22 of FIG. 7. The attachment system includes a pair of identical buckles 90 and a pair of identical strap members 91. The buckles 90 and the strap members 91 are attached to the four attachment pads 44 on the shell 22.

Each buckle 90 has a first end 77, a second end 78, and sides 79 extending between the ends. A generally rectangular-shaped slot 93 is formed in each buckle 90. The slot 93 is off-set toward the second end 78 and positioned so that the long dimension of the slot extends toward the sides 79. A first surface 84 of each buckle 90 is formed with a grouping 94 of hooks. The grouping 94 is desirably positioned generally between the slot 93 and the first end 77. A second surface 85, which is opposite the first surface 84, and a perimeter 89 of the first surface, are desirably although not necessarily free of hooks.

The strap members 91 are each formed of a stretchable material and have a looped face 48 and an opposite face 49. Each strap member 91 also has forward and rearward end portions 46 and 47. A hook patch 75 of single-sided hook material is attached by ultrasonic bonds, adhesives, stitches or other suitable means adjacent each end portion 46 and 47. The hook patches 75 desirably contain a unidirectional hook material with the machine direction of the hooks aligned with the longitudinal axis of the strap member 91 and the hooks facing toward a center portion of the strap member.

This attachment system (see FIGS. 10 & 11) is used in nearly the same manner as the attachment system described in relation to FIGS. 7-9. In this system, however, the strap member 91 is releasably attached to the buckle 90 by the hook-and-loop connection between the looped face 48 and the hook patch 75, which is located at the forward end portion 46 of the strap member. The forward end 46 and the hook patch 75 are inserted through the slot 93, and the strap member 91 is folded back onto itself so that the hook patch can releasably engage the looped face 48. The effective length of the strap member 91 may be adjusted by releasing the hook patch 75 from the looped face 48, and either increasing or decreasing the amount of the strap member that extends through the slot 93. In all other respects, this attachment system functions similar to that described in relation to the embodiment of FIGS. 7-9. The grouping 94 of hooks on the buckle 90 releasably engages an attachment pad on the front waist section 28, and the hook patch 75 near the rearward end 47 releasably engages an attachment pad on the back waist section 29.

In the attachment system illustrated in FIGS. 10 and 11, the two hook patches 75 are attached to the looped face 48 of each strap member 91. One alternate design is to attach the hook patch 75 on the forward end portion 46 to the looped face 48, but to attach the hook patch 75 on the rearward end portion to the opposite face 49. In use, the forward end portion 46 would then be inserted through the slot 93 from the first surface 84 to the second surface 85, and the hook patch 75 on the forward end portion would be attached to the looped face 48.

A wide variety of materials may be used to construct the aforementioned components of the garments (20 in FIG. 1; 60 in FIG. 6; and 70 in FIG. 7). The backing sheet 24, for example, may comprise a thin, substantially liquid impermeable web or sheet of plastic film such as polyethylene, polypropylene, polyvinyl chloride or similar material. The backing sheet material may be transparent or opaque and have an embossed or matte surface. One preferred material for the backing sheet 24 is a polyethylene film that has a nominal thickness of about 0.001 inch and a systematic matte embossed pattern, and that has been corona treated on both sides. Alternately, the backing sheet 24 may comprise a nonwoven, fibrous web which has been suitably constructed and arranged to be substantially liquid impermeable.

The bodyside liner 25 may be any soft, flexible, porous sheet which passes fluids therethrough. The bodyside liner 25 may comprise, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The bodyside liner 25 has a pore size that readily allows the passage therethrough of liquids, such as urine and other body exudates. The liner 25 may be selectively embossed or perforated with discrete slits or holes extending therethrough. Optionally, the web or sheet may be treated with a surfactant to aid in liquid transfer. One preferred bodyside liner material is a wettable spunbonded polypropylene having a basis weight of 0.7 ounces per square yard. Such material may be produced by the methods and apparatus described in U.S. Pat. Nos. 4,340,563 and 4,405,297 to Appel et al., which are incorporated herein by reference.

The absorbent core 26 is preferably an air-formed batt of cellulosic fibers (i.e., wood pulp fluff). One preferred type of wood pulp fluff, which is available under the trade designation CR2054 from Kimberly-Clark Corporation of Neenah, Wis., is a bleached, highly absorbent sulphate wood pulp containing softwood fibers. Optionally, the absorbent core 26 could comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers.

The absorbent core 26 may also include compounds to increase its absorbency, such as an effective amount of organic or inorganic high-absorbency materials. For example, the absorbent core 26 can include 0-95 weight percent high-absorbency material. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacylamides, polyvinyl pyridine and the like. Other suitable polymers can include hydrolyzed acrylonitrile grafted starch, acrylic acid grafted starch, and isobutylene maleic anhydride copolymers, and mixtures thereof. The hydrogel polymers are preferably sufficiently cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Celanese Corporation, and Allied-Colloid. Typically, the high-absorbency material is capable of absorbing at least about 15 times its weight in water, and preferably is capable of absorbing more than about 25 times its weight in water.

The high-absorbency material can be distributed or otherwise incorporated into the absorbent core 26 employing various techniques. For example, the high-absorbency material can be substantially uniformly distributed among the fibers comprising the absorbent core. The materials can also be nonuniformly distributed within the absorbent core fibers to form a generally continuous gradient with either an increasing or decreasing concentration of high-absorbency material, as determined by observing the concentration moving inward from the backing sheet 24. Alternatively, the high-absorbency material can comprise a discrete layer separate from the fibrous material of the absorbent core 26, or can comprise a discrete layer integral with the absorbent core.

Absorbent core 26 may also include a tissue wrap layer to help maintain the integrity of the fibrous core. This tissue wrap typically comprises a hydrophilic cellulosic material, such as creped wadding or a high wet-strength tissue.

The elastic strands 32 may be formed of a dry-spun coalesced multifilament elastomeric thread sold under the tradename LYCRA and available from I.E. Du Pont de Nemours and Company. Alternately, the leg elastic members 33 may be formed of other typical elastics utilized in the diaper-making art, such as a thin ribbon of natural rubber. Elasticity could also be imparted to the longitudinal side sections by extruding a hot melt elastomeric adhesive between the backing sheet 24 and the bodyside liner 25. Other suitable elastic gathering means are disclosed in U.S. Pat. Nos. 4,938,754 to Mesek and 4,388,075 to Mesek et al.

The foregoing detailed description has been for the purpose of illustration. Thus, a number of modifications and changes may be made without departing from the spirit and scope of the present invention. For example, the strap members 40 and attachment pads 44 could be formed with identical loop material, and the two surfaces of the adapter elements 42 could be formed with different hook materials. One of the surfaces, intended to attach to the strap members 40 (or the patches 66), could be formed with a more aggressive hook material. One skilled in the art would recognize that a more aggressive hook material may comprise a material with a greater average hook height, a greater percent of directionally-aligned hooks, or a more aggressive hook shape. Likewise, the attachment system may be associated with garments other than the disposable absorbent garments as described herein. Therefore, the invention should not be limited by the specific embodiments described, but only by the claims.

We claim:

1. A garment comprising:
   a garment shell having opposite first and second longitudinal ends, a first waist section adjacent the first longitudinal end and a second waist section adjacent the second longitudinal end;
   attachment pads located in the first waist section, the attachment pads separated from one another and positioned adjacent the first longitudinal end;
   strap members independent of the shell each having an inner surface and an opposite surface; and
   adapter elements independent of the strap members and the shell each having opposite first and second surfaces, the first surface adapted to releasably engage one of the attachment pads and the second surface adapted to releasably engage the inner surface of one of the strap members such that each of the adapter elements is adapted to be positioned between one of the attachment pads and one of the strap members to secure the shell by means of the strap members about a wearer.

2. The garment according to claim 1, wherein a first force required to release the first surface from one of the attachment pads is less than a second force required to release the second surface from the inner surface of one of the strap members.

3. The garment according to claim 1, wherein:
   the attachment pads comprise a plurality of loop members;
   the first and second surfaces of the adapter elements comprise a plurality of hook members; and
   the inner surfaces of the strap members comprise a plurality of loop members.

4. The garment according to claim 3, wherein the strap members are formed of a stretchable material.

5. The garment according to claim 1, wherein the strap members are attached to the second waist section.

6. A garment for use by a wearer, comprising:
   a garment shell having opposite first and second longitudinal ends, a first waist section adjacent the first longitudinal end, a second waist section adjacent the second longitudinal end, and a crotch section between the first and second waist sections;
   strap members independent of the shell for securing the shell to the wearer, each strap member having an inner surface and an opposite surface;
   attachment pads located in the first waist section, the attachment pads separated from one another and positioned adjacent the first longitudinal end;
   adapter elements independent of the shell and the strap members each having opposite first and second surfaces, the first surface adapted to releasably engage one of the attachment pads and the second surface adapted to releasably engage the inner surface of one of the strap members such that each of the adapter elements is adapted to be positioned between one of the attachment pads and one of the strap members to secure the shell by means of the strap members about a wearer; and means for releasably attaching the strap members to the second waist section.

7. The garment according to claim 6, wherein the first and second surfaces of the adapter elements are substantially identical.

8. The garment according to claim 7, wherein the first and second surfaces of the adapter elements comprise a plurality of hook members.

9. The garment according to claim 8, wherein the first and second surfaces of the adapter elements include generally flat perimeter portions.

10. The garment according to claim 6, wherein the strap members and the attachment pads comprise a loop material.

11. The garment according to claim 10, wherein a first force required to release the first surface from one of the attachment pads is less than a second force required to release the second surface from the inner surface of one of the strap members.

12. The garment according to claim 6, wherein the means for releasably attaching the strap members to the second waist section comprises:

at least one additional attachment pad attached to the second waist section; and at least one additional adapter element, the additional adapter element having a first surface adapted to releasably engage the additional attachment pad and a second surface adapted to releasably engage the strap members.

13. A garment comprising:

a garment shell having a first waist section and a second waist section;

a strap member independent of the shell;

an adapter element independent of the shell and the strap member having opposite first and second surfaces, the first surface adapted to releasably engage the first waist section and the second surface adapted to releasably engage the strap member such that the adapter element is adapted to be positioned between the first waist section and the strap member to secure the shell by means of the strap member about a wearer, wherein a first force required to release the first surface from the first waist section is less than a second force required to release the second surface from the strap member.

14. The garment according to claim 13, wherein the first and second surfaces of the adapter element are substantially identical.

15. The garment according to claim 14, wherein the first and second surfaces of the adapter element comprise a plurality of hook members.

16. A garment comprising:

a garment shell having a first waist section and a second waist section;

an attachment pad attached to the first waist section;

a buckle independent of the shell adapted to releasably engage the attachment pad, the buckle defining a slot therein;

a strap member independent of the shell and the buckle having a first face, a second face opposite the first face, a first end sized to fit through the slot, and releasably attached to the buckle and a second end;

means for releasably attaching a portion of the strap member adjacent the first end to the buckle; and means for releasably attaching a portion of the strap member adjacent the second end to the second waist section.

17. The garment of claim 16, wherein a portion of the buckle defining the slot is formed with a toothed pattern.

18. The garment of claim 16, wherein the buckle includes a grouping of hooks adapted to releasably engage the attachment pad.

19. The garment of claim 18, wherein the strap member includes a hook patch adjacent the first end, the hook patch adapted to releasably attach the portion of the strap member adjacent the first end to the buckle.

20. The garment of claim 16, wherein the first face of the strap member comprises a hook material.

21. The garment of claim 16, wherein the means for releasably attaching the portion of the strap member adjacent the second end to the second waist section comprises a hook patch attached to the second end, the hook patch adapted to releasably engage the second waist section.

22. The garment of claim 16, wherein:

the buckle comprises a primary grouping of hooks adapted to releasably engage the attachment pad;

the buckle comprises a secondary grouping of hooks adapted to releasably attach the portion of the strap member adjacent the first end to the buckle; and the slot is positioned between the primary and secondary groupings of hooks.

23. A garment comprising:

a garment shell having a first waist section and a second waist section;

an attachment pad formed of a loop material and attached to the first waist section;

a pair of buckles independent of the shell each comprising a grouping of hooks adapted to releasably engage the attachment pad and each defining a slot therein;

a pair of strap members independent of the shell and the buckle each having a first face, a second face opposite the first face, a first end sized to fit through the slot, and releasably attached to the buckle and a second end;

means for releasably attaching a portion of each strap member adjacent the first end to one of the pair of buckles; and means for releasably attaching a portion of each strap member adjacent the second end to the second waist section.

* * * * *